United States Patent [19]

MacCuish

[11] Patent Number: 5,674,845
[45] Date of Patent: Oct. 7, 1997

[54] TREATMENT OF INSULIN-RESISTANT DIABETES

[75] Inventor: Angus Carstairs MacCuish, Glasgow, Great Britain

[73] Assignee: Fujisawa Pharmaceutical Co., Ltd., Osaka, Japan

[21] Appl. No.: 412,222

[22] Filed: Mar. 27, 1995

Related U.S. Application Data

[63] Continuation of Ser. No. 829,004, filed as PCT/GB90/01399, Sep. 10, 1990, abandoned.

[30] Foreign Application Priority Data

Sep. 8, 1989 [GB] United Kingdom ............... 8920381

[51] Int. Cl.$^6$ ............... A61K 37/36; A61K 37/26
[52] U.S. Cl. ............... 514/12; 514/21
[58] Field of Search ............... 514/12, 21

[56] References Cited

FOREIGN PATENT DOCUMENTS

| | | |
|---|---|---|
| 0331630 | 9/1989 | European Pat. Off. |
| 0360411 | 3/1990 | European Pat. Off. |

OTHER PUBLICATIONS

Diabetic, Journal of the British Association, Supplement of vol. 5, p. 7, 1988, J. D. Quin, et al., "A25. Mendenhall's Syndrome—A Therapeutic Dilemma".

The New England Journal of Medicine, vol. 317, No. 3, pp. 137–140, Jul. 16, 1987, Hans–Peter Guler, M.D., et al., "Short–Term Metabolic Effects of Recombinant Human Insulin–Like Growth Factor in Healthy Adults".

Diabetes/Metabolism Reviews, vol. 1, Nos. 1 & 2, pp. 189–191, 1985, S. I. Taylor, "Receptor Defects in Patients with Extreme Insulin Resistance".

The New England Journal of Medicine, vol. 317, No. 3, 16 Jul. 1987, H.P. Guler et al.: "Short–term metablic effects of recombinant human insulin–like growth factor I in healthy adults", pp. 137–140.

Diabetologia, vol. 31, 1988, Diabetologia Springer–Verlag, Pub., N. Livingston et al.: "Characterisation of insulin–like growth factor 1 receptor in skeletal muscles of normal and insulin resistant subjects", pp. 871–877.

*Primary Examiner*—Cecilia J. Tsang
*Assistant Examiner*—P. Lynn Touzeau
*Attorney, Agent, or Firm*—Oblon, Spivak, McClelland, Maier & Neustadt, P.C.

[57] ABSTRACT

Insulin-like growth factor (IGF) is used for treatment of type A insulin-resistant diabetes by reduction of glucose levels. The treatment is applicable to Mendenhall's Syndrome, Werner Syndrome, leprechaunism, lipoatrophic diabetes, and other lipoatrophies.

11 Claims, 1 Drawing Sheet

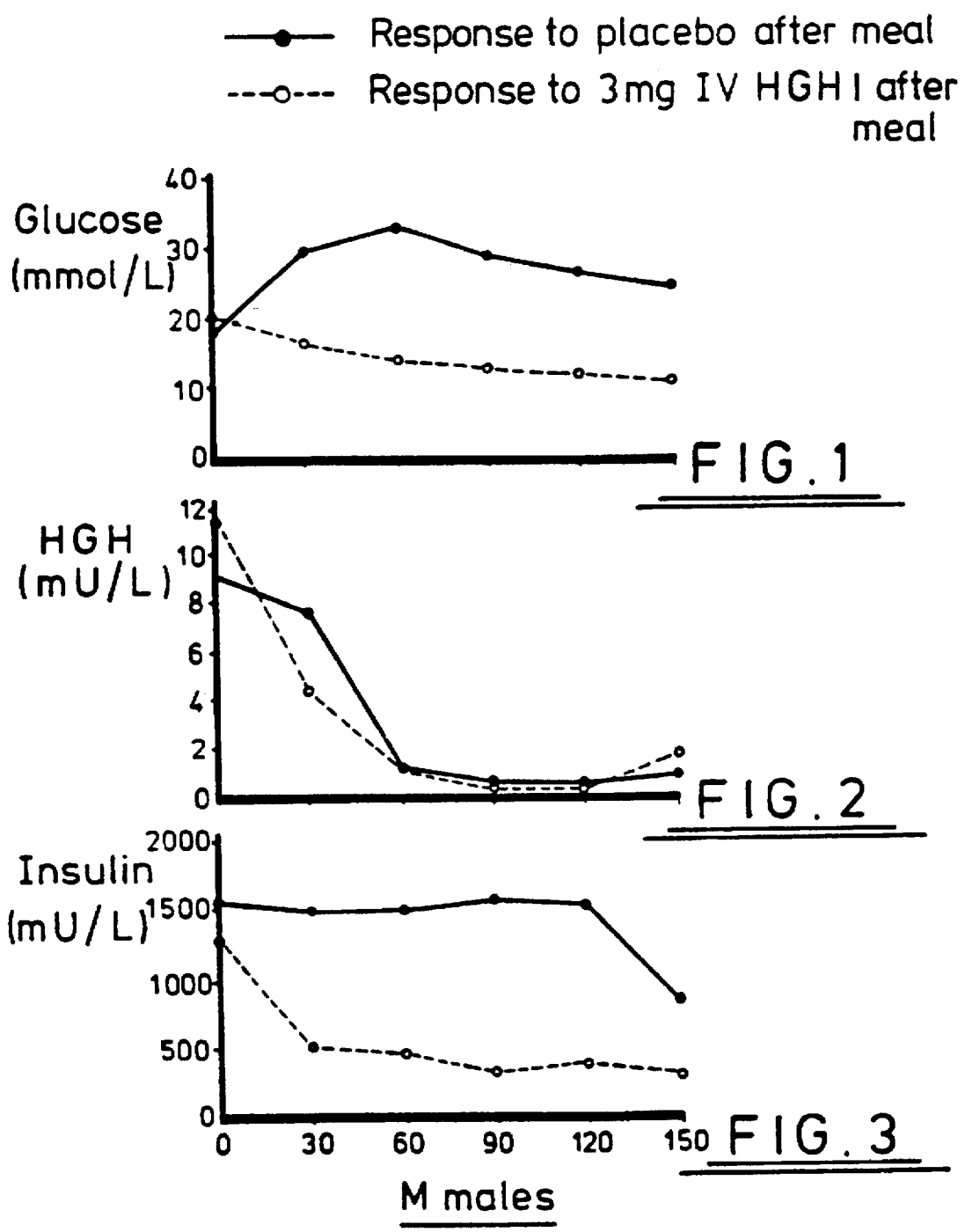

1

TREATMENT OF INSULIN-RESISTANT DIABETES

This application is a continuation of application Ser. No. 07/829,004, filed May 8, 1992, now abandoned, which was filed as International Application No. PCT/GB90/01399, filed on Sep. 10, 1990.

TECHNICAL FIELD

The present invention relates to the treatment of insulin-resistant diabetes. In this rare condition, hyperglycaemia (elevated blood glucose) does not respond to administered insulin, possibly due to a genetic abnormality in the cellular insulin receptor which prevents insulin from performing its normal role.

BACKGROUND

The syndrome which bears his name was first described by Mendenhall in 1950 in three children from one family. All developed insulin-resistant diabetes when aged about 7 years and subsequently died in ketoacidotic coma. Several constant somatic abnormalities were noted, including early dentition, facial dysmorphism and tonsillar hypertrophy which predisposed to the development of middle ear sepsis. The children had enlarged external getitalia with abdominal protuberance and in common with other insulin-resistant states, acanthosis nigricans was observed. Pineal hyperplasia was found at post-mortem, the cause remaining obscure.

In 1975 the syndrome was described in two siblings from a family in the UK. One died at the age of 7 years, in the other, emergency hypophysectomy was performed and proved to be life-saving when the child developed ketoacidotic coma. The cause of insulin-resistant diabetes in this distressing syndrome was subsequently examined by Taylor et al in a further patient and marked decrease in the cellular binding of insulin was demonstrated by in-vitro culture of cell lines from child. Thus Mendenhall's syndrome is regarded as analogous to other rare forms of diabetes with acanthosis nigricans, i.e. type A insulin resistance where functional/structural impairment of the insulin receptor B submit results from an abnormality of the insulin in receptor gene.

Further examples of type A insulin resistance would be Werner Syndrome in women, leprecornism, lipoatrophic diabetes and other lipoatrophies.

In the light of those observations, it is not surprising that conventional antidiabetic therapies (dietary manipulation, oral hypoglycaemics, insulin injections) have been entirely ineffective in the Mendenhall syndrome. Young patients with the Mendenhall and similar rare syndromes are at high risk of death from ketoacidotic coma if their state of chronic and gross hyperglycaemia is further adversely affected by physiological events ( e.g. puberty, menstruation) or added pathology (e.g. infection).

IGF-1 has structural similarities to proinsulin. However, its cell receptor is different to that of insulin. IGF has been investigated for its potential growth-enhancing effects on farmed animals. It has also been admininstered to patients having Laron - type dwarfism (Laron Z. et al. Lancet 1988; 2; 1170–2).

A process for the production of IGF-1, involving synthesis through the use of recombinant DNA technology, is described in EP-A-0219814. The resulting recombinant IGF-1 is identical in terms of its amino acid composition to naturally occurring human IGF-1.

EP-A-0308386 describes a method for improving the regeneration of transected peripheral nerves in mammals and man, for instance following damage by an accident or surgery, which comprises administering IGF-1. JP-A-63/196524 relates to a permucosal absorptive carcinostatic action regulator comprising (a) a growth factor, such as IGF-1, and (b) an absorption accelerator.

EP-A-0289584 discloses a wound healing and bone regenerating composition which comprises a mixture of purified platelet-derived growth factor and purified IGF-1. The composition may be used in the healing of external wounds in mammals and is said to act by promoting growth of epithelial and connective tissues and the synthesis of total protein and collagen. EP-A-0237514 describes enhancing the growth of mammary parenchyma in mammals by the intra-mammary administration of a mitogenic agent, such as IGF-1.

EP-A-0209331 relates to the extraction of pure bovine IFG-1 and its use as an animal growth promoter. FR-A-2533438 refers to the use in cosmetic preparations of various growth factors, such as IGF-1, which have been shown to have a mitogenic action on human or animal skin cells. EP-A-0104933 describes a method for growth promotion and feed efficiency improvement which involves the continuous intravenous or subcutaneous administration of IGF-1.

SUMMARY OF THE INVENTION

It is an object of the present invention to provide a treatment for insulin-resistant diabetes.

The present invention relates to the therapeutic use of insulin-like growth factor (IGF) for the treatment of type-A insulin-resistant diabetes.

The invention also provides a method of treatment of a patient having type-A insulin-resistant diabetes which comprises the administration of a therapeutically effective amount of insulin-like growth factor.

The invention further provides the use of insulin-like growth factor for the manufacture of a medicament for the treatment of type-A insulin-resistant diabetes.

Insulin-like growth factors are known and occur naturally in the body. Whilst the present invention is primarily concerned with IGF-1, IGF-2 (which is about ten times more potent) may also be employed. The IGF may be made using recombinant DNA techniques in view of its more ready availability. The IGF protein structure may be identical to the native product or differ from it by additions, deletions or replacements which leave unaffected its cell receptor binding properties and glucose-reducing effect.

The IGF is usually administered intravenously, subcutaneously or intramuscularly in a dosage such as to provide a target blood plasma level of 50–150 micrograms per kg. This intravenous injection is usually at a nominal dosage rate of 3–6 mg/kg body weight. By analogy to known dose-response relationships for insulin, corresponding dosages for subcutaneous and intramuscular administration can be derived. Since IGF has a short halflife in-vivo, administration by intravenous injection may need to be repeated several times a day. Subcutaneous injection has a more extended duration and may be administered less frequently e.g. twice daily.

The IGF may be formulated for extended release by combination with suitable agents (haptens, zinc etc) conventionally used for insulin.

REFERRED EMBODIMENT

An embodiment of the present invention will now be described by way of example only.

CASE REPORT

The patient was the second child of healthy non-consanguineous parents and was born at 44 weeks' gestation after an uneventful pregnancy. He weighed 2.5 kg. at birth and was noted to have abdominal distension, an enlarged phallus and facial dysmorphism. Diabetes mellitus was diagnosed at age 7 years and initial treatment, by dietary/carbohydrate restriction, was unsuccessful. Subsequent therapeutic trials of an oral sulphonylurea (Tolbutamide) and a biguanide (Metformin) were equally ineffective. The injection of subcutaneous insulin (up to 100 units per day) had no appreciable effect on either mean daily blood glucose or glycated haemoglobin level (14.2%, laboratory normal 8%).

By the age of 13 years, he had an established metabolic pattern of gross, chronic hyperglycaemia and intermittent ketonuria. The patient's endogenous levels of IGF-1 were subnormal for his age.

METHODS

Plasma insulin and C-peptide were measured using standard radio-immunoassay (RIA) procedures described previously (1). Plasma IGF-1 was measured using the RIA kit supplied by Nichols Institute Diagnostics, San Juan, Calif.; serum growth hormone was determined using an in-house immunoradiometric) assay standardised against the First International Reference Preparation of human growth hormone (MRC 66/217; 2 mu =1. ug). Insulin binding status was assessed by platelet binding techniques (2,3 ). IGF-1 was donated by the Fujisawa Pharmaceutical Company, synthesised by recombinant DNA technology and had an aminoacid sequence identical to that of native human IGF-1 (4). Lyophilised IGF-1 was dissolved in normal saline and injected as a single intravenous bolus of 3 mgm (100 ug/kg) after breakfast. Venous blood was withdrawn for analysis through an indwelling catheter at 0, 2, 5, 15, 30, 60, 120, and 180 minutes after injection. Further boluses of 6 and 12 mgm respectively were subsequently given in the fasted state with hormonal profiles measured after the latter dose. A further experiment was performed with a 12 mgm intravenous bolus of IGF-1 given before breakfast and followed by hourly hormonal sampling until 5 p.m. For purposes of comparison, the hormonal response to standard meals was measured and a 75 G oral glucose tolerance test was performed after an overnight fast.

RESULTS

Initial IGF-1 level prior to therapy was subnormal at 0.2 ku/l (normal 0.5 to 4.0 ku/l, corrected for sex and age). Insulin binding status was examined and found to be impaired (Table 1). Oral glucose tolerance testing (75 G load) confirmed marked hyperglycaemia with gross hyperinsulinaemia (Table 2). Following a 3 mgm intravenous bolus of IGF-1, given post prandially, blood glucose fell to a nadir of 11.2 mmols/l after 120 minutes (FIG. 1). Plasma insulin declined rapidly from 1290 to 315 mu/l (FIG. 3), C-peptide from 1.92 to 0.88 nmols/l and HGH from 11.2 to 0.5 mu/l (FIG. 2). Also given for comparison is the response to a placebo (intravenous isotonic saline bolus) in insulin, C-peptide, HGH and blood glucose following a standard hospital breakfast (carbohydrate content 50 G). Similar findings were observed following a 6 mgm intravenous bolus; and after a 12 mgm bolus, given in the fasting state, blood glucose declined to 8.3 mmols/l. Thereafter boluses of 12 mgm IGF-1 were given intravenously before breakfast and lunch: mean blood glucose over an 8-hour period was 17.4 mmols/l and mean plasma insulin 290.2 mu/l. By comparison, a mean blood glucose of 29.1 mmols/l and mean plasma insulin of 769 mu/l was observed over the same time period when no therapy was given.

REFERENCES

1. Small M, Cohen HN, Beastall GH, MacCuish AC. Comparison of oral glucose loading and intravenous glucagon injection as stimuli to C-peptide secretion in normal men. Diabetic Med 1985; 2:181–3
2. Hajek AS, Joist JH, Baker RK et al. Demonstration and partial characterisation of insulin receptors in humam platelets. J. Clin Invest 1979; 63:1060–5
3. Udvardy M, pfiegler G, Rak K. Platelet insulin receptor determination in non-insulin dependent diabetes mellitus. Experientia 1985; 41: 422–33.
4. Niwa M, Sato S, Saito Y et al. Chemical synthesis, cloning and expression of genes for human somatomedin C (insulin-like growth factor 1) and 59Val-somatomedin C. Ann NY Acad Sci 1986; 469: 31–52.

TABLE 1

| Insulin concentration in supernatant (ng/ml) | Specific insulin binding (pg. $2 \times 10^8$ platelets) | |
|---|---|---|
| | PATIENT | CONTROLS |
| 0.1 | 0.27 | $0.37 \pm 0.09$ |
| 0.2 | 0.35 | $0.62 \pm 0.17$ |
| 0.6 | 1.48 | $1.70 \pm 0.45$ |
| 1.0 | 1.48 | $2.73 \pm 0.83$ |

Insulin receptor status (insulin binding) of platelets from patients and controls determined by in vitro assay.

TABLE 2

| Time (min) | Glucose | HGH | Insulin | C-peptide |
|---|---|---|---|---|
| 0 | 11.7 | 0.9 | 407 | 2.3 |
| 30 | 18.9 | 0.6 | 510 | 5.5 |
| 60 | 30.1 | 0.5 | 1600 | 10.2 |
| 90 | 29.9 | 0.7 | 934 | 4.1 |
| 120 | 24.4 | 6.9 | 726 | 3.9 |

Blood glucose and hormone levels after oral glucose loading (75 g), following an overnight fast. Glucose in mmol/l; HGH and insulin in mU/l; C-peptide in nmol/l.

I claim:

1. A method of treating insulin-resistant diabetes, comprising administering a therapeutically effective amount of insulin-like growth factor to a patient in need thereof.

2. The method of claim 1, wherein said insulin-resistant diabetes is Mendenhall's syndrome.

3. The method of claim 1, wherein said insulin-resistant diabetes is type A insulin-resistant diabetes.

4. The method of claim 1, wherein said insulin-resistant diabetes is selected from the group consisting of Werner Syndrome, leprechaunism and lipotrophic diabetes.

5. The method of claim 1, wherein said insulin-like growth factor is insulin-like growth factor-1.

6. The method of claim 5, wherein said therapeutically effective amount provides a target blood plasma level of insulin-like growth factor-1 of 50–150 micrograms per kilogram.

7. The method of claim 1, wherein said therapeutically effective amount is 3–6 milligrams per kilogram.

8. The method of claim 1, wherein said insulin-like growth factor is administered intravenously, subcutaneously, or intramuscularly.

9. The method of claim 8, wherein said insulin-like growth factor is administered intravenously, several times a day.

10. The method of claim 8, wherein said insulin-like growth factor is administered subcutaneously, twice daily.

11. The method of claim 1, further comprising administering haptens or zinc to said patient.

* * * * *